United States Patent
Casado-Chaudanson et al.

(10) Patent No.: US 9,198,850 B2
(45) Date of Patent: *Dec. 1, 2015

(54) COSMETIC USE OF ORGANIC RESINATES

(75) Inventors: Audrey Marjorie Casado-Chaudanson, Aubagnen (FR); Audrey Celine Marcelle Pastor, Antibes (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 709 days.

This patent is subject to a terminal disclaimer.

(21) Appl. No.: 12/531,162

(22) PCT Filed: Mar. 14, 2008

(86) PCT No.: PCT/EP2008/053109
§ 371 (c)(1), (2), (4) Date: Sep. 14, 2009

(87) PCT Pub. No.: WO2008/110628
PCT Pub. Date: Sep. 18, 2008

(65) Prior Publication Data
US 2010/0021415 A1    Jan. 28, 2010

Related U.S. Application Data

(60) Provisional application No. 60/941,741, filed on Jun. 4, 2007.

(30) Foreign Application Priority Data

Mar. 14, 2007 (FR) ..................................... 07 01840

(51) Int. Cl.
| | | |
|---|---|---|
| A61K 31/74 | (2006.01) |
| A61K 8/81 | (2006.01) |
| A61Q 15/00 | (2006.01) |
| A61Q 17/00 | (2006.01) |
| A61Q 19/00 | (2006.01) |

(52) U.S. Cl.
CPC ............. *A61K 8/8117* (2013.01); *A61K 8/8147* (2013.01); *A61Q 15/00* (2013.01); *A61Q 17/00* (2013.01); *A61Q 19/00* (2013.01); *A61K 2800/54* (2013.01)

(58) Field of Classification Search
USPC ........................................................ 424/78.1
See application file for complete search history.

(56) References Cited

U.S. PATENT DOCUMENTS

| | | | |
|---|---|---|---|
| 2,653,902 A | | 9/1953 | Thurmon |
| 2,951,012 A | | 8/1960 | Gisvold |
| 5,804,168 A | * | 9/1998 | Murad ............................ 424/59 |
| 6,333,093 B1 | * | 12/2001 | Burrell et al. ................. 428/194 |
| 2004/0223944 A1 | * | 11/2004 | Capelli ........................ 424/78.1 |
| 2005/0255048 A1 | * | 11/2005 | Hirsh et al. ..................... 424/44 |

FOREIGN PATENT DOCUMENTS

| | | |
|---|---|---|
| DE | 1 050 507 B | 2/1959 |
| DE | 1 095 992 B | 12/1960 |
| JP | 60-218312 A | 11/1985 |
| WO | WO 93/07862 A1 | 4/1993 |
| WO | WO 0170194 A1 * | 9/2001 |
| WO | WO 02/49588 A2 | 6/2002 |

OTHER PUBLICATIONS

International Search Report dated Dec. 2, 2008.

* cited by examiner

*Primary Examiner* — Dennis J Parad
(74) *Attorney, Agent, or Firm* — Young & Thompson (57) ABSTRACT

A cosmetic method for releasing an active principle in a controlled fashion to uninjured skin, as a function of the ion content in or on skin, by exchange with the ions, in order to provide at least one cosmetic benefit to the skin, the method includes applying onto skin a composition containing, in a cosmetically acceptable medium, at least one resinate including one organic ion-exchange resin and at least one ionizable cosmetic active principle bonded in noncovalent fashion to the resin.

10 Claims, 2 Drawing Sheets

COSMETIC USE OF ORGANIC RESINATES

The present invention relates to a cosmetic method for releasing an active principle in a controlled fashion to uninjured skin, as a function of the ion content in or on skin, by exchange with said ions, in order to provide at least one cosmetic benefit to the skin, said method comprising applying onto skin a composition containing, in a cosmetically acceptable medium, at least one resinate including one organic ion-exchange resin and at least one ionizable cosmetic active principle bonded in noncovalent fashion to said resin.

Ion-exchange resins are insoluble macromolecules carrying ionizable groups which have the property of reversibly exchanging some of their ions on contact with other ions originating from a solution. These resins have a certain capacity to retain ions (expressed per gram of dry resin) which corresponds to the number of millimoles (mmol) of ions which the resin can exchange per unit of weight. In addition, ion-exchange resins are characterized by the size of their particles and by the pK of their functional group.

More particularly, anion-exchange resins, also known as anionic resins or basic resins, carry positively charged functional groups and have the property of reversibly exchanging some of their anions on contact with other anions, such as $Cl^-$, $OH^-$, $SO_4^{2-}$, and the like.

The positively charged functional groups are attached to the support of the resins, which can either be inorganic (for example of zeolite type) or organic (for example of cholestyramine type, including styrene and divinylbenzene monomer units). The following are distinguished among the functional groups of anionic resins: quaternary or tertiary amino groups, which are characteristic of strong anionic resins, and secondary and primary amino groups, which are characteristic of weak anionic resins.

Analogously, cation-exchange resins, also known as cationic resins or acidic resins, carry negatively charged functional groups and have the property of reversibly exchanging some of their cations on contact with other cations, such as $Na^+$, $H^+$, $Ca^{2+}$, and the like.

There exist cationic resins including styrene and divinylbenzene or acrylic monomer units which have sulfonic functional groups, characterizing strong cationic resins (for example, Amberlite® IRP88, Amberlite® IRP69, Dowex®, and the like), or carboxylic functional groups, characterizing weak cationic resins (for example, Amberlite® IRP64).

The use is already known of ion-exchange resins in making possible controlled release of pharmaceutical and/or cosmetic active principles in and/or on the body.

In particular, application US 2004/0146384 describes a complex comprising an anionic resin, for example of cholestyramine type, and a cosmetic active principle, such as an anti-wrinkle agent, an exfoliant or an antioxidant, which makes possible the controlled release of this active principle administered orally.

Application US 2004/0223944 describes a resinate comprising an anion-exchange resin, for example of cholestyramine type, and an antimicrobial silver thiosulfate complex applied topically to a wound using a dressing impregnated with said resinate.

In U.S. Pat. No. 7,788,055, dextromethorphan, an antitussive, is released in a controlled manner by virtue of the trapping thereof in a cationic resin.

U.S. Pat. No. 5,837,226 describes the controlled release of pharmaceutical active principles in the eye via microspheres comprising an ion-exchange resin and preferably a cation-exchange resin.

Application US 2005/0255048 discloses a topical formulation in the form of a foam or spray comprising a water-soluble active principle and a fat-soluble active principle, at least one of the active principles of which is bonded to an ion-exchange resin. The release of the active principle bonded to the resin takes place in the presence of moisture on the skin.

U.S. Pat. No. 6,033,655 describes formulations for moisturizing the skin comprising cosmetic and/or pharmaceutical active principles and also anionic or cationic resins to which magnetic particles are bonded.

Document DE-1 095 992 describes the use of resines loaded with pentathionates to manufacture solid compositions for skin treatment.

Finally, US application No. US 2005/00586672 describes zeolites, inorganic exchangers of ions, which make possible controlled release of cosmetic and/or pharmaceutical active principles present in a cosmetic composition, by application of this composition to the skin.

However, the functional groups (in particular of the quaternary ammonium type) of zeolites are not covalently bonded to the inorganic matrix, which weakens the bonding of the anionic active principle to the zeolite and thus consequently the stability of the zeolite/active principle complex. This results in possible exchanges of ions between the anionic compounds present in the composition and that absorbed in the zeolite, which restricts the latitude for formulation of these compositions in the case where it is desired to administer a specific anionic active principle to the skin. Furthermore, one of the distinguishing features of zeolites is that of absorbing the moisture present on the skin, so that they do not make possible controlled release of the active principles into or on the skin as a function of the ionic content thereof.

The majority of the ions present in or on the skin are provided by eccrine sweat, which has the highest water content of any sweat of the body, since it is composed of approximately 99% water. The ions contained in sweat lie usually within the following concentration ranges (in mM/l): $Na^+$: 24-56; $Cl^-$: 18-54; $K^+$: 3-7; $HCO_3^-$: 0,4-2,5; lactate: 6, 5-13 (Patterson et al., *Expt. Physiol.* 85:869-875, 2000). The presence of these ions on skin may, inter alia, be measured by means of specific electrodes or according to a conventional method using filter paper (Grice et al., *British Journal of Dermatology*, 92:511-518, 1975). The other ions present in or on skin are essentially, on the one hand, those produced by sebaceous glands and, on the other hand, those present in the NMF. The NMF contains lactate ions and inorganic ions, in particular potassium. It has been shown that the presence of lactate ions is correlated with skin hydration state (Noriaki et al., *J. Invest. Dermatol.*, 122:3, 755-763, 2004).

Now, it would be most desirable to provide a system for entrapping cosmetic active principles which would enable them to be released in a controlled fashion as a function of the ion content on skin. It would thus be possible to increase the release rate of active principle into or on skin when it sweats due to a change in temperature which may be due to exercise, heat, seasons, stress or emotions, for instance. This would enable to provide, for instance, a concentration of photoprotecting agent or slimming agent which would be high enough even when skin sweats.

Alternatively, such a system could allow to release an increasing amount of anti-bacterial, anti-seborrheic, anti-inflammatory/soothing or keratolytic agent to skin when sebum production by sebaceous glands increases.

Lastly, it would be interesting to be able to have a means allowing to dispense a moisturizing agent on skin in a higher amount at the day times when skin Trans-Epidermal Water Loss (TEWL) is the highest, when it thus tends to dry more.

Indeed, studies (LE FUR et al., J.I.D. Vol. 117, No. 3, pp. 718-724) have shown that TEWL was subject to circadian rythms and that it was the highest around 8 am and 4 pm. However, it is hardly conceivable to think of re-applying during the day, at fixed hours, a moisturizing cosmetic composition.

Consequently, the need remains to provide a carrier allowing to stably entrap, by strong bonds, a cosmetic active principle and to release into or on skin an amount of this active principle that is automatically adjusted to skin ion content and varies therewith, as a function of phenomena that may change skin ionic composition, such as a function of sweat, sebum production or TEWL value, without having to carry out successive applications of the composition containing this carrier, including during exercise or throughout the day.

In point of fact, the Applicant Company has now discovered that it is possible to use at least one organic resinate to deliver, in controlled fashion, an ionizable cosmetic active principle to skin in an amount which increases as a function of its content of ions.

The subject of this invention is thus a cosmetic method for releasing an active principle in a controlled fashion to uninjured skin, as a function of the ion content in or on skin, by exchange with said ions, in order to provide at least one cosmetic benefit to the skin, said method comprising applying onto skin a composition containing, in a cosmetically acceptable medium, at least one resinate including one organic ion-exchange resin and at least one ionizable cosmetic active principle bonded in noncovalent fashion to said resin.

The method according to the invention is preferably carried out on uninjured skin. The term "uninjured skin" is understood to mean healthy (nonpathological) skin, that is to say devoid of wounds, injuries or other lesions modifying the anatomical features (forms) or physiological features (functions) thereof. The method according to the invention is preferably conducted on sweating skin and/or on people subject to exercise and/or to heat.

In the context of the present invention, the term "resinate" is understood to mean a complex composed of at least one organic ion-exchange resin and of at least one ionizable cosmetic active principle. The active principle is bonded to the resin in a non-covalent fashion, i.e. by noncovalent bonds only. The term "noncovalent bond" is understood to mean an ionic bond, which is the bond caused by the transfer of one or more valence electrons (of the outer electron shell) between a donor atom belonging to the cosmetic active principle and another recipient atom belonging to the resin.

The term "cosmetically acceptable medium" is understood to mean a physiologically acceptable medium, that is to say a medium compatible with the skin which does not result in unacceptable feelings of discomfort (red blotches, tightness, tingling, and the like) for the user after application to the skin.

The formation of the resinates according to the invention is carried out by conventional techniques for the absorption of ionic active principles on ion-exchange resins. These techniques generally comprise three main stages: a first stage, which consists of a pretreatment of the resin, a second stage, which comprises the absorption proper of the active principle on the resin, and a third stage, which comprises the washing of the resinate obtained.

The stage of pretreatment of the resin consists in making available the exchanging sites of the resin and in removing constituents of the resin which might be exchanged subsequently. This operation can be carried out in particular by suspending the resin in various media, such as in water, in an aqueous solution comprising sodium hydroxide or in other solvents.

The stage of absorption of active principles comprises suspending the dry pretreated resin or the crude resin in an aqueous and/or alcoholic solution comprising one or more cosmetic active principles. It is at the end of this stage that the substitution between counterions of the resin and cosmetic active principles is carried out.

The washing stage consists in removing the active principle not bonded to the resin. It is generally carried out using a medium in which the active principle is soluble, such as an aqueous and/or alcoholic solution.

After these three stages, a resinate is obtained. The level of active principle on the resinate is defined as the weight of active principle with respect to the weight of resinate and remains entirely dependent on the type of resin, on the type of active principle, on the conditions for treating the resin and on the conditions for absorption of the active principle on the resin. These resinates can be incorporated in a composition in order to be administered to the skin.

According to an alternative form, the resinates are formed by the absorption of ionic active principles on ion-exchange resins within the actual cosmetic composition.

Preferably, the level of absorption of an active principle on the resin will be 1-100% of the exchange capacity of this resin, as indicated in patent application US 2002/0146384.

When the resinates are brought into contact with the skin, and more specifically with the ions present in or on it, they release the cosmetic active principle or principles at the surface of the skin. This release of active principles can be quantified as set out below.

The greater the number of ions in or on skin and the greater the degree of release of cosmetic active principles on the skin. These ions may for instance be chosen among sodium, chloride, potassium, lactate ions and their mixtures.

In addition, the level of absorption of the cosmetic active principle or principles on the resin has an influence on the degree of release of these. This is because the greater the level of absorption of active principles, the greater the degree of release.

The kinetics of release are immediate but it is possible to modify them, to prolong them, to control them or to delay them by coating the resin with water-soluble or fat-soluble polymers. Such polymers are cited in U.S. Pat. No. 5,837,226, such as, in particular, cellulose derivatives (ethylcellulose, cellulose acetate, and the like), polyurethanes, methacrylate-based polymers or copolymers, polycaprolactones, polyesters, and the like.

In a preferred embodiment, the organic ion-exchange resin is an organic anionic resin having a styrene/divinylbenzene matrix, such as those sold under the brands Amberlite® IRA404 Chloride by Röhm & Haas, Dowex® 2*8 Chloride by Dow Chemical Co., Dowex® 1*8 Chloride by Dow Chemical Co. and Dowex® 1*2 Chloride by Dow Chemical Co.

According to another preferred embodiment, the organic ion-exchange resin is an organic anion-exchange resin comprising a copolymer including acrylic and divinylbenzene monomer units, such as that sold under the brand Amberlite® IRA67 by Röhm & Haas.

According to an even more preferred embodiment, the organic anion-exchange resin is a resin comprising a copolymer including styrene and divinylbenzene monomer units with quaternary ammonium functional groups, also known as cholestyramine and sold in particular under the brand Duolite® AP143/1093 by Röhm & Haas. The exchangeable anion of this resin is the chloride anion.

According to another preferred embodiment, the organic ion-exchange resin is an organic cationic resin comprising a copolymer including styrene and divinylbenzene monomer units, such as, for example, the resin sold under the brand Amberlite® IR122 Na, or a resin comprising a copolymer including acrylic and divinylbenzene monomer units, such as, for example, the resin sold under the brand Amberlite® IRC86.

In another preferred embodiment, an organic anionic resin, such as the resin Duolite® AP143/1093, is used in combination with an organic cation-exchange resin, such as Amberlite® IR122 Na or Amberlite® IRC86.

The term "cosmetic active principles" is understood to mean the compounds authorized to be used as such according to European regulations and in particular according to Directive 76/768/EEC, its annexes and its amending acts.

The cosmetic active principles which can be trapped in the ionic resins according to the invention combine all the cosmetic active principles which can be applied to the skin and which have ionizable groups. Mention may be made, for example, of acids of AHA (α-hydroxy acid) type, such as glycolic acid, lactic acid, citric acid, malic acid, mandelic acid, tartaric acid and gluconic acid; β-hydroxy acids, such as salicylic acid and its derivatives, such as 5-(n-octanoyl) salicylic acid; phenolic acids, such as ferulic acid, gallic acid, chlorogenic acid, rosmarinic acid, caffeic acid and vanillic acid; sunscreens, such as ensulizole, phenyl-benzimidazole-sulfonic acid, sold under the brands Parsol® HS or Eusolex® 232, PABA (4-aminobenzoic acid), ecamsule (terephthalylidenedicamphorsulfonic acid), sulisobenzone (benzophenone-4) and benzophenone-5 (2-hydroxy-4-methoxy-benzophenone-5-sulfonic acid); carboxylic acids, such as tannic acid, lipoic acid, aleuritic acid, arjunolic acid, fumaric acid, oleanolic acid, phytic acid, ursolic acid, usnic acid, pyrrolidonecarboxylic acid (PCA), madecassic acid and Asiatic acid; vitamins, such as ascorbic acid (vitamin C), nicotinic acid (vitamin PP), pantothenic acid (vitamin B5) and folic acid (vitamin B9); alcohols, such as phenylethyl alcohol, forskolin and quercetin; escin; and the like.

Pyrrolidone carboxylic acid, zinc, vanillic acid and escin are preferred for a use in the present invention.

In one embodiment, the ionizable cosmetic active principle bonded in noncovalent fashion to said ionic resin is chosen from agents having cosmetic properties, such as, for example, moisturizing agents, antiwrinkle agents or antioxidants, firming or slimming agents, sunscreens (photoprotective agents), skin depigmenting agents, antibacterial agents, antiseborrheic agents, keratolytic agents, antiperspirant agents, soothing agents, astringent agents, perfuming agents, and their mixtures.

The cosmetic benefit obtained according to the invention depends on the cosmetic active principle or principles used. It comprises in particular the moisturizing of the skin, the smoothing of wrinkles and/or fine lines, the firming of the skin, antisun protection, the reduction in perspiration and/or unpleasant odors, the reduction in sebaceous secretion or comedons, the alleviation of cutaneous discomfort, such as red blotches and/or tightness and/or tingling, the depigmenting and slimming of the body, which comprises in particular the slimming treatment of excess weight, for example of the thighs and hips, and the alleviation of cellulite and/or the orange peel effect.

The composition according to the invention can be provided in any formulation form and in particular in the form of an oil-in-water (O/W), water-in-oil (W/O) or multiple (W/O/W, O/W/O, and the like) emulsion or gel. Advantageously, it is provided in the form of an oil-in-water emulsion.

The composition according to the invention can comprise various adjuvants, such as at least one compound chosen from:
- oils, which can be chosen in particular from: volatile or nonvolatile, linear or cyclic, silicone oils, such as polydimethylsiloxanes (dimethicones), polyalkylcyclosiloxanes (cyclomethicones) and polyalkylphenylsiloxanes (phenyl dimethicones); synthetic oils, such as fluorinated oils, alkyl benzoates and branched hydrocarbons, such as polyisobutylene; vegetable oils, in particular soybean oil or jojoba oil; and mineral oils, such as liquid paraffin;
- waxes, such as ozokerite, polyethylene wax, beeswax or carnauba wax;
- silicone elastomers, in particular obtained by reaction, in the presence of a catalyst, of a polysiloxane having at least one reactive group (hydrogen or vinyl, in particular) and carrying at least one end and/or side alkyl (in particular methyl) or phenyl group with an organosilicon, such as an organohydropolysiloxane;
- surfactants, preferably emulsifying surfactants, whether nonionic, anionic, cationic or amphoteric, in particular esters of fatty acids and of polyols, such as esters of fatty acids and of glycerol, esters of fatty acids and of sorbitan, esters of fatty acids and of polyethylene glycol and esters of fatty acids and of sucrose; ethers of fatty alcohols and of polyethylene glycol; alkylpolyglucosides; and polysiloxanes modified by polyethers; betaine and its derivatives; polyquaterniums; ethoxylated fatty alcohol sulfate salts; sulfosuccinates; sarcosinates; alkyl and dialkyl phosphates and their salts, such as potassium cetyl phosphate; and soaps of fatty acids;
- cosurfactants, such as linear fatty alcohols and in particular cetyl and stearyl alcohols;
- thickening agents and/or gelling agents, in particular crosslinked or noncrosslinked, hydrophilic or amphiphilic, homo- and copolymers of acryloylmethylpropanesulfonic acid (AMPS) and/or of acrylamide and/or of acrylic acid and/or of salts or esters of acrylic acid; xanthan or guar gum; cellulose derivatives; and silicone gums (dimethiconol);
- humectants, such as polyols, including glycerol, propylene glycol and sugars, and glycosaminoglycans, such as hyaluronic acid and its salts and esters;
- organic screening agents, such as dibenzoylmethane derivatives (including butyl methoxydibenzoyl-methane), cinnamic acid esters (including ethylhexyl methoxycinnamate), salicylates, β,β-diphenylacrylates, triazines and phenylbenzo-triazoles;
- inorganic screening agents, based on inorganic oxides in the form of pigments or nanopigments, which may or may not be coated, and in particular based on titanium dioxide or zinc oxide;
- preservatives;
- fillers, in particular powders with a soft-focus effect, which can be chosen in particular from polyamides, silica, talc, mica or fibers (in particular polyamide or cellulose fibers);
- tightening agents, in particular plant proteins, synthetic latexes and colloidal dispersions of inorganic fillers;
- sequestering agents, such as EDTA salts;
- fragrances;
- and their mixtures, without this list being limiting.

Examples of such adjuvants are mentioned in particular in the CTFA Dictionary (International Cosmetic Ingredient Dictionary and Handbook, published by The Cosmetic, Toiletry and Fragrance Association, 11$^{th}$ Edition, 2006).

In addition to the active principles entrapped in the organic resin, the composition used according to the invention can comprise other active principles and in particular at least one active principle chosen from: agents which stimulate the production of growth factors; agents stimulating the expression of tensin 1, FN3K and/or FN3K RP; antiglycation or deglycating agents; agents which enhance the synthesis of collagen or which prevent its decomposition (anticollagenase agents, in particular matrix metalloproteinase inhibitors); agents which enhance the synthesis of elastin or which prevent its decomposition (antielastase agents); agents which enhance the synthesis of glycosaminoglycans or proteo-glycans or which prevent their decomposition; agents which enhance the proliferation or differentiation of keratinocytes; agents which enhance the proliferation of fibroblasts; depigmenting, antipigmenting or propigmenting agents; antioxidants, agents for combating free radicals or agents for combating pollution; agents which enhance the synthesis of epidermal lipids; agents which stimulate lipolysis, which inhibit lipogenesis and/or which inhibit the differentiation of adipocytes; draining or detoxifying agents or agents which improve the microcirculation; and their mixtures, without this list being limiting.

Examples of such additional active principles are in particular: plants extracts and in particular extracts of *Butea frondosa, Magnolia champaca, Vanilla planifoliai, Cedrus atlantica, Canarium commune, Zingiber cassumunar, Chondrus crispus*, of *Thermus thermophilus*, of *Pisum sativum*, of *Centella asiatica*, of *Sphacelaria scoparia*, of *Scenedesmus*, of *Moringa pterygosperma*, of ivy (*Hedera helix*), of *Castanea sativa*, of *Hibiscus sabdriffa*, of *Polyanthes tuberosa*, of *Argania spinosa*, of seeds of *Hibiscus esculentus*, of *Narcissus tarzetta*, of licorice or of *Ruscus esculatus*; an essential oil of *Citrus aurantium* (Neroli); silicon derivatives, such as methylsilanol mannuronate; plant protein hydrolysates (in particular soybean or hazelnut protein hydrolysates); sugars; acylated oligopeptides, sold in particular by Soderma under the trade names Maxilip®, Matrixyl® 3000, Biopeptide® CL or Biopeptide® EL or described in application EP-1 449 517; yeast extracts and in particular *Saccharomyces cerevisiae* extracts; algal extracts and in particular extracts of *laminaria* species and of *Blidingia minima*; caffeine and coffee and mate extracts comprising it; vitamins and their derivatives, such as retinyl palmitate, ascorbyl glucoside, ascorbyl palmitate, ascorbyl tetraisopalmitate, ascorbyl sorbate, tocopherol, tocopheryl acetate and tocopheryl sorbate; methacryloyloxyethylphosphorylcholine homo- and copolymers; urea; ceramides and phospholipids; arbutin; tranexamic acid esters; dihydroxyacetone (DHA); erythrulose; and their mixtures.

The composition in accordance with the present invention can be presented in the forms conventionally used for a topical application to the skin, that is to say in the form of a gel, cream, lotion, spray, foam, patch, milk, mask or ointment, comprising normal compatible excipients and carriers which are cosmetically acceptable.

The invention will now be illustrated by the following nonlimiting examples and by reference to the attached drawings in which.

EXAMPLES

A. In Vitro Tests

Example 1

Examples of the Pretreatment of Anionic Resins

Condition 1.1:
20 g of Duolite® AP143/1093 resin (supplier: Röhm & Haas) are suspended in 200 g of water, stirring is carried out and then the suspension is allowed to separate by settling in order to remove the supernatant. The operation of washing with demineralized water is repeated approximately 10 times. The same operation is subsequently carried out with a 10% NaCl solution (likewise approximately 10 times), and then rinsing is carried out with demineralized water. Subsequently, the wet resin is dried in a ventilated oven at 35° C. overnight.
Condition 1.2:
20 g of Duolite® AP143/1093 resin (supplier: Röhm & Haas) are suspended in 200 g of water comprising 10% NaOH, stirring is carried out and then the suspension is allowed to separate by settling in order to remove the supernatant (the operation is repeated approximately 10 times). Rinsing is then carried out twice with demineralized water and the wet resin is dried in a ventilated oven at 35° C. overnight.

The pretreatment stage is not compulsory.

Example 2

Examples of the Absorption of Active Principles on the Resin

Condition 2.1
The Solution for the Absorption of Active Principles Comprises 3% of Escin, an Anionic Active Principle
Approximately 1.2 g of crude Duolite® AP143/1093 resin are suspended in 60 g of aqueous solution comprising 3% of escin. Stirring is carried out for approximately 12 hours, washing is carried out with demineralized water, the supernatant is removed and the resin, charged with escin, is dried in order to obtain an escin resinate. The supernatant is assayed before and after absorption by liquid chromatography/mass spectroscopy (LC/MS). The amount of escin charged is approximately 35%.
Condition 2.2
The Solution for the Absorption of Active Principles Comprises 3% of Escin and Potassium Hydroxide
Approximately 1.2 g of crude Duolite® AP143/1093 resin are suspended in 60 g of aqueous solution comprising 3% of escin and 0.19% of KOH (pH of approximately 5). Stirring is carried out for approximately 2 hours, washing is carried out with demineralized water, the supernatant is removed and the resin, charged with escin, is dried in order to obtain an escin resinate. The supernatant is assayed before and after absorption by LC/MS. The amount of escin charged is approximately 50%.
Condition 2.3
The Solution for the Absorption of Active Principles Comprises 70% of Glycolic Acid, an Anionic Active Principle
Approximately 1.2 g of dry resin pretreated according to condition 1.1 are suspended in 18 g of aqueous solution comprising 70% of glycolic acid and 4% of KOH. Stirring is carried out for approximately 1 hour, washing is carried out with demineralized water, the supernatant is removed and the resin, charged with glycolic acid, is dried. The amount of charged glycolic acid on the resin was not evaluated.
Condition 2.4
The Solution for the Absorption of Active Principles Comprises 0.5% of Cobalamin, a Cationic Active Principle Approximately 1.2 g of crude Amberlite® IRP64 resin are suspended in 60 g of aqueous solution comprising 0.5% of cobalamin. Stirring is carried out for approximately 1 hour, washing is carried out with demineralized water, the supernatant is removed and the resin, charged with cobalamin, is dried. The amount of charged cobalamin on the resin was not evaluated.
Condition 2.5
The Solution for the Absorption of Active Principles Comprises 3% of Zinc, a Cationic Active Principle Approximately 2 g of crude Amberlite® IRP 69 resin are suspended in 100 g of aqueous solution comprising 3% of zinc. Stirring is carried out for approximately 2 hours, the supernatant is removed and the resin, charged with zinc, is dried. The zinc resinate thus obtained is mineralized and then analyzed by ICP/MS. The amount of charged zinc is about 12%.
Condition 2.6
The Solution for the Absorption of Active Principles Comprises 2% of Escin, an Anionic Active Principle Approximately 1.2 g of a 35% charged escin resinate is suspended in 60 g of aqueous solution comprising 2% of escin. Stirring is carried out for approximately 2 hours, the supernatant is removed and the resin, charged with escin, is dried. The supernatant is dosed before and after absorption, by liquid chromatography/mass spectroscopy (LC/MS). The amount of final charged escin is about 55%.

Many other conditions can be envisaged by varying various parameters, such as the temperature, the pressure, the continuous absorption, the contacting time, and the like. These conditions can influence the level of active principle charged. Generally, for a batch process as described in the examples (nonlimiting as depending on the process), the level of resin in the solution for the absorption can vary from 1 to 25%. The percentage of active principle in the absorption solution is a function of its solubility.

For all the conditions mentioned above in the absorption examples, the washing operations were carried out with a demineralized aqueous solution until the washing solutions no longer comprised free active principle or only a very small percentage.

Various washing solutions are possible. They are chosen according to the type of resin, the nature of the active principle to be treated and the release media envisaged. In addition, the number of washing operations necessary can vary greatly according to the active principles.

Example 3

Release Examples

Condition 3.1
Influence of the Release Medium

Resin subjected to absorption condition 2.3 is suspended in various ionic and nonionic media. The release solutions are assayed by UV spectroscopy. The weight of glycolic acid in these solutions is evaluated in order to have a degree of release of glycolic acid (Degree in %=weight of glycolic acid assayed/weight of glycolic acid resinates×100).

The degrees of release as a function of the various media studied appear below:
Demineralized water: 0-0.5%
0.05% NaCl: 4-5%
0.1% NaCl: 5-6%
0.1% $CaCl_2$: 8-9%
0.9% NaCl: 18-19%
10% NaCl: 25-26%
pH 7: 12% (buffer solution with $Na_2HPO_4$ and $KH_2PO_4$ to obtain the pH)
pH 5.5: 10% (buffer solution with $Na_2HPO_4$ and $KH_2PO_4$ to obtain the pH)

It is found that the release is virtually zero in a demineralized medium.

In addition, the greater the content of ions in the release medium, the greater the release. The 0.05% and 0.1% conditions are close to the true values of salts in sweat.
Condition 3.2
Influence of the Absorption Conditions Resins subjected to various absorption conditions (2.1 and 2.2) are suspended in various ionic and nonionic media. The release solutions are assayed by LC/MS. The weight of escin in these solutions is evaluated in order to have a degree of release of escin (Degree in %=weight of escin assayed/weight of escin resinate×100).

|  | 2.1 | 2.2 |
| --- | --- | --- |
| Demineralized water | 0-0.5% | 0-0.5% |
| 10% NaCl | 14-16% | 23-25% |

It is found that the more the amount of escin present on the resinate increases, the more the level of escin released increases.

The results obtained for other cosmetic active principles under various absorption conditions and using a Duolite® AP143/1093 resin pretreated with a mixture of water and 10% NaCl are summarized in table 1 below.

TABLE 1

| | | Experimental conditions of the absorption | | | | | | |
| --- | --- | --- | --- | --- | --- | --- | --- | --- |
| Cosmetic active principle tested | Resin/level absorption solution | Nature of the absorption medium | Concentration of absorption solution | KOH concentration in the absorption solution | Absorption time | Degree released/Resins | | |
| | | | | | | Water | 0.9% NaCl | 10% NaCl |
| Vanillic acid | 2% | Water/ethanol (50/50) | 5% | 2% | 3 H | 0.4% | 22% | 31% |
| Lactic acid | 2% | Water | 10% | 4.2% | 1 H | 0.5% | 20% | 28% |

TABLE 1-continued

| | | | Experimental conditions of the absorption | | | | | |
|---|---|---|---|---|---|---|---|---|
| Cosmetic active principle tested | Resin/level absorption solution | Nature of the absorption medium | Concentration of absorption solution | KOH concentration in the absorption solution | Absorption time | Degree released/Resins | | |
| | | | | | | Water | 0.9% NaCl | 10% NaCl |
| Gluconic acid | 2% | Water | 10% | 0% | 1 H | 0.3% | 10% | 23% |
| Citric acid | 2% | Water | 10% | 4% | 1 H | 0.5% | 17% | 31% |
| Ascorbic acid | 2% | Water | 10.1% | 4% | 30 min | 0.90% | 20% | 26% |
| Gallic acid | 2% | Water | 8% | 2% | 2 H | 0.1% | 10% | 24% |

These results confirm that the richer the medium is in chloride ions, the greater is the degree of release of active principles.

Condition 3.3

Study of the Sustained Release of Vanillic Acid in the Presence of a Constant Salt Amount One conducts the following in vitro protocol for the purpose of simulating a sustained and continuous release on skin.

On skin, the mean content of salts is about 0.05%. This content changes and is constantly renewed all day long, under standard conditions.

In the protocol below, a step of changing the release medium has been introduced in order to represent in vitro this phenomenon.

About 0.1 g of vanillic acid resinate is suspended in 3 g of aqueous solution containing 0.05% NaCl. Stirring is carried out for about 1 minute by means of a vortex, then the supernatant and the resinate are separated by centrifugation. The whole supernatant is removed therefrom, filtrated then dosed by liquid chromatography (LC).

3 g of an aqueous solution containing 0.05% NaCl are added again onto the resinate described above. The mixing, separating and dosing protocol described above is repeated.

This latter step is repeated 10 times.

Figure 1:
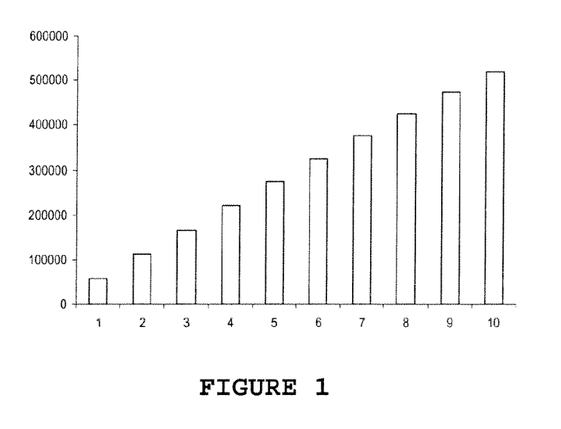
FIG. 1 illustrates the release rate of vanillic acid by contacting a resinate with ten successive solutions of chloride ions.
Figure 2:
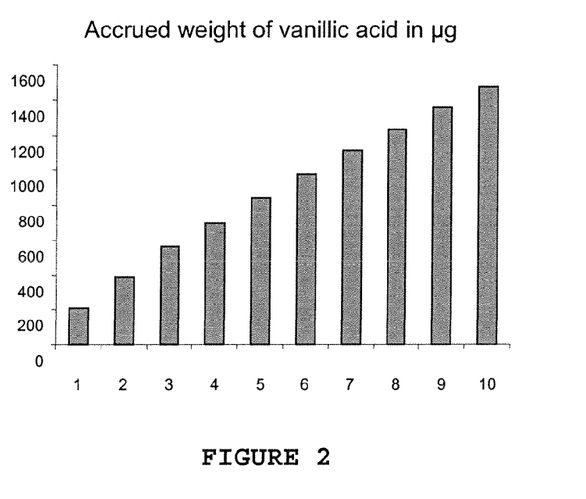
FIG. 2 illustrates the release rate of vanillic acid by contacting a resinate with ten successive solutions of lactate ions.

The results obtained are shown on FIG. 1 and may also translate into the following Table:

| Release | Mean accrued areas |
|---|---|
| 1 | 58233 |
| 2 | 112900 |
| 3 | 166567 |
| 4 | 220700 |
| 5 | 273867 |
| 6 | 325933 |
| 7 | 376367 |
| 8 | 425400 |
| 9 | 473433 |
| 10 | 519767 |

For each renewal of the solution, a constant release of vanillic acid is observed.

These results demonstrate that the resinates such as vanillic acid resinate allow a gradual release of active principle on skin by exchange with its ions, all day long, under standard conditions.

Condition 3.4

Study of the Sustained Release of Vanillic Acid in the Presence of a Constant Sodium Lactate Amount The protocol followed is the same as that described under Condition 3.3.

About 0.1 g of vanillic acid resinate is suspended in 3 g of aqueous solution containing 0.05% of sodium lactate. Stirring is carried out for about 1 minute by means of a vortex, then the supernatant and the resinate are separated by centrifugation. The whole supernatant is removed therefrom, filtrated and then dosed by UV spectroscopy.

3 g of an aqueous solution containing 0.05% of sodium lactate are added again onto the resinate described above. The mixing, separating and dosing protocol described above is repeated.

This latter step is repeated 10 times.

The area under the curve of UV absorption is measured. The results obtained are shown on FIG. 1 and may also translate into the following Table:

| Release | Accrued weight of vanillic acid in µg |
|---|---|
| 1 | 207 |
| 2 | 384 |
| 3 | 562 |
| 4 | 697 |
| 5 | 841 |
| 6 | 978 |
| 7 | 1113 |
| 8 | 1233 |
| 9 | 1352 |
| 10 | 1470 |

For each renewal of the solution, a constant release of vanillic acid is observed.

These results demonstrate that the resinates such as vanillic acid resinate allow a gradual release of active principle on skin by exchange with its ions, all day long, under standard conditions.

B—In Vivo Tests

1. Study of the Release of an Active Principle as a Function of Sweat

A gel comprising both free vanillic acid and resinates composed of Duolite® AP143/1093 resin complexed to vanillic acid molecules and a gel comprising solely free vanillic acid are applied to the backs of 5 subjects on either side of the spinal column, with this being done on different days.

Six regions are distinguished, from which samples are withdrawn using a sorbent material provided in the form of narrow flexible strips, at the following withdrawal times: T45, T75, T105, T180, T240 and T300 (times in minutes). A sample withdrawn at T15 acts as control for each region.

All the sample withdrawals are repeated three times.

After extracting the narrow strips used for withdrawing the samples, the vanillic acid is quantified by HPLC, the conditions for which are as follows:

System Agilent LC1000,

Column Zorbax RP18 15×4.6 mm. 3.5 μm,

Water/methanol gradient analysis,

Flow rate 0.2 ml/min,

Detection 260 nm, and injection 5 μl.

A comparative study is carried out on the amount of vanillic acid available on the skin after application, on the one hand, of a control gel comprising 0.07% of free vanillic acid and, on the other hand, of a gel comprising free vanillic acid and vanillic acid complexed to the Duolite® AP143/1093 resin. The latter gel is obtained using 0.07% of free vanillic acid and 1% of vanillic acid resinates (comprising approximately 25-30% of vanillic acid).

The study kinetics are produced over a period of 5 hours, it being known that two sports sessions (step sessions), each of 15 minutes, took place before the sample withdrawals T75 and T300 and that a session of exposure to the sun lasting 15 minutes took place before the sample withdrawal T180.

Figure 3:
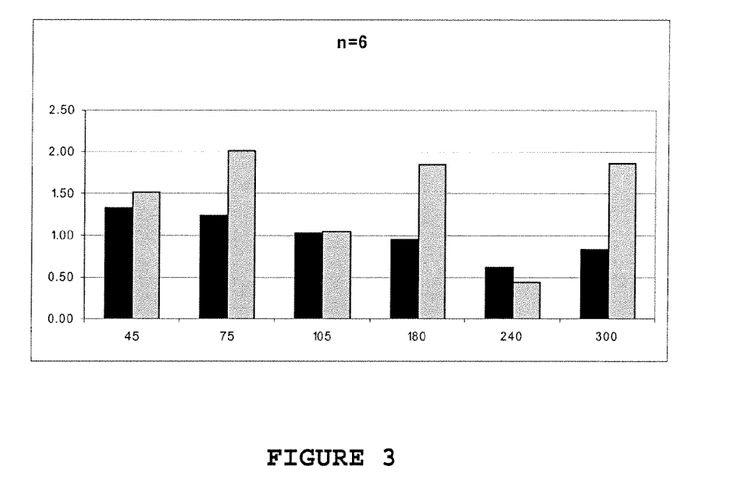
FIG. 3 illustrates the release kinetics of vanillic acid as a function of time, after application onto a person subject to an exercise session.

A graph representing the percentage of active principle available as a function of time is appended in FIG. 3.

It is found that the percentage of vanillic acid available on the skin is substantially constant after application of the control gel.

On the other hand, after application of the gel comprising the resinates, the percentage of vanillic acid available on the skin greatly increases during the periods preceded by sports sessions (the percentage of active principle available changes, from T45 to T75, respectively from 131% to 242% and then, from T240 to T300, respectively from 71% to 200%) or by exposure to the sun (the percentage of active principle available changes, from T105 to T180, respectively from 114% to 205%). The value of the preceding percentages corresponds to the mean value obtained for the 5 subjects.

These results confirm the fact that the anionic resin exchanges the negatively charged active principle with the anions present on the skin, all the more so as the amount of sweat on the skin increases.

2. Study of the Release of an Active Principle as a Function of the TEWL

The same protocol as described under B.1 is conducted, except that one includes measurements of the Trans-Epidermal Water Loss (TEWL) at each withdrawal time. The study was conducted on 6 subjects.

Figure 4:
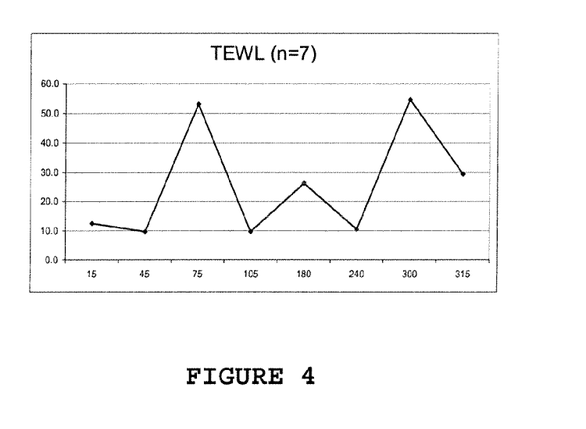
FIG. 4 illustrates TEWL evolution under the same conditions as on FIG. 3.

FIG. 4 illustrates the evolution of TEWL as a function of the various withdrawal times.

For the times T=75, T=180 and T=300 min, higher TEWL values are observed.

Comparing this TEWL evolution with the results shown on FIG. 3, it appears that at the withdrawal times when the TEWL is higher, the percentage of vanillic acid on skin is higher after applying the gel with the resinates.

C—Cosmetic Compositions

The following compositions were prepared in a way conventional to a person skilled in the art. The amounts of ingredients mentioned below are shown as percentage by weight. The resinates are formed from Duolite® AP143/1093.

Example C-1

Gel

| | |
|---|---|
| Gelling agent | 0.50% |
| Base | 0.38% |
| Preservative | 0.40% |
| Vanillic acid resinate | 5.00% |
| Demineralized water | 93.72% |

Example C-2

Oil-in-Water Emulsion

| | |
|---|---|
| Butylene glycol | 5.0% |
| Gelling agent | 0.2% |
| Emulsifier | 4.0% |
| Coemulsifier | 0.2% |
| Preservative | 1.0% |
| Oils | 8.0% |
| Antioxidant | 0.3% |
| Base | 0.2% |
| pH adjuster | 0.1% |
| Vanillic acid resinate | 5.0% |
| Demineralized water | 76.0% |

Example C-3

Slimming Cream-Gel, Hydroalcoholic O/W Emulsion

| | |
|---|---|
| Gelling/emulsifying agent | 1.30% |
| Glycol | 14.00% |
| Glycerin | 5.00% |
| Gelling agent | 0.20% |
| Oil | 8.00% |
| pH adjuster | 0.60% |
| Chelating agent | 0.05% |
| Coloring agent | 0.20% |
| Powders | 0.10% |
| Essential oil | 0.30% |
| *PLECTRANTHUS BARBATUS* ROOT EXTRACT[i] | 0.03% |
| *ZINGIBER CASSUMUNAR* ROOT EXTRACT[ii] | 0.006% |
| RUSCOGENIN[iii] | 0.10% |
| METHYLSILANOL MANNURONATE[iv] | 3.00% |
| ESCIN[v] | 0.40% |
| GLAUCINE[vi] | 2.50% |
| Escin resinate | 0.40% |
| Mineral water | 33.80% |
| Alcohol | 20.00% |

[i]Forskolin ®, INDENA
[ii]Purple Bengle ®, BIOLANDES
[iii]INDENA
[iv]Algisium C ®, EXSYMOL
[v]INDENA
[vi]Bodyfit ®, SEDERMA

What is claimed is:

1. A cosmetic method for gradually releasing an amount of active principle on skin by exchange with ions of said active principle, all day long, under standard conditions, in order to provide at least one cosmetic benefit to the skin, said method comprising applying onto skin a composition consisting of, in a cosmetically acceptable medium, at least one resinate including one organic ion-exchange resin and at least one ionizable cosmetic active principle bonded in noncovalent fashion to said resin, wherein the ionizable cosmetic active principle bonded in noncovalent fashion to said resin is selected from the group consisting of glycolic acid as an anionic active principle, cobalamin as a cationic active principle, lactic acid as an anionic active principle, gluconic acid as an anionic active principle, citric acid as an anionic active principle, ascorbic acid as an anionic active principle, gallic acid as an anionic active principle, pyrrolidonecarboxylic acid as an anionic active principle, zinc as a cationic active principle, vanillic acid as an anionic active principle and escin as an anionic active principle, and wherein the cosmetic benefit is selected from the group consisting of smoothing wrinkles and/or fine lines, firming the skin, reduction in perspiration and/or unpleasant odors, reduction in sebaceous secretion or comedons, alleviation of cutaneous discomfort selected from the group consisting of red blotches, tightness, tingling and combinations thereof, depigmenting, slimming of the body and a keratolytic effect.

2. The method as claimed in claim 1, wherein the organic ion-exchange resin is an organic anion-exchange resin.

3. The method as claimed in claim 2, wherein the organic anion-exchange resin comprises a copolymer including styrene and divinylbenzene monomer units.

4. The method as claimed in claim 2, wherein the organic anion-exchange resin comprises a copolymer including acrylic and divinylbenzene monomer units.

5. The method as claimed in claim 1, wherein the organic ion-exchange resin is an organic cation-exchange resin.

6. The method as claimed in claim 5, wherein the organic cation-exchange resin comprises a copolymer including styrene and divinylbenzene monomer units.

7. The method as claimed in claim 5, wherein the organic cation-exchange resin comprises a copolymer including acrylic and divinylbenzene monomer units.

8. The method as claimed in claim 1, wherein use is made of a combination of organic anion-exchange resin and of organic cation-exchange resin.

9. The method according to claim 1, which is carried out on sweating skin.

10. The method according to claim 9, which is carried out on people subject to exercise and/or heat.

* * * * *